US00PP37835P2

(12) United States Plant Patent
Grazzini

(10) Patent No.: US PP37,835 P2
(45) Date of Patent: Nov. 3, 2026

(54) ***DIANTHUS* PLANT NAMED 'G21002'**

(50) Latin Name: *Dianthus hybrida*
Varietal Denomination: G21002

(71) Applicant: Richard A. Grazzini, Columbus, OH (US)

(72) Inventor: Richard A. Grazzini, Columbus, OH (US)

(73) Assignee: GARDENGENETICS LLC, Columbus, OH (US)

( * ) Notice: Subject to any disclaimer, the term of this patent is extended or adjusted under 35 U.S.C. 154(b) by 0 days.

(21) Appl. No.: 19/412,446

(22) Filed: Dec. 8, 2025

(51) Int. Cl.
*A01H 5/02* (2018.01)
*A01H 6/30* (2018.01)

(52) U.S. Cl.
USPC ..... Plt./278

(58) Field of Classification Search
USPC ..... Plt./272, 273, 278
See application file for complete search history.

(56) References Cited

U.S. PATENT DOCUMENTS

PP36,710 P2 * 5/2025 Grazzini ..... Plt./273

* cited by examiner

*Primary Examiner* — Susan Mccormick Ewoldt
(74) *Attorney, Agent, or Firm* — C. Anne Whealy

(57) ABSTRACT

A new and distinct cultivar of *Dianthus* plant named 'G21002', characterized by its compact and mounding plant habit; vigorous growth habit and rapid growth rate; freely branching habit; dense and bushy appearance; dark green-colored leaves; freely flowering habit; relatively large single-type dark scarlet red-colored flowers; and good garden performance and winter hardiness.

2 Drawing Sheets

Figure 1:
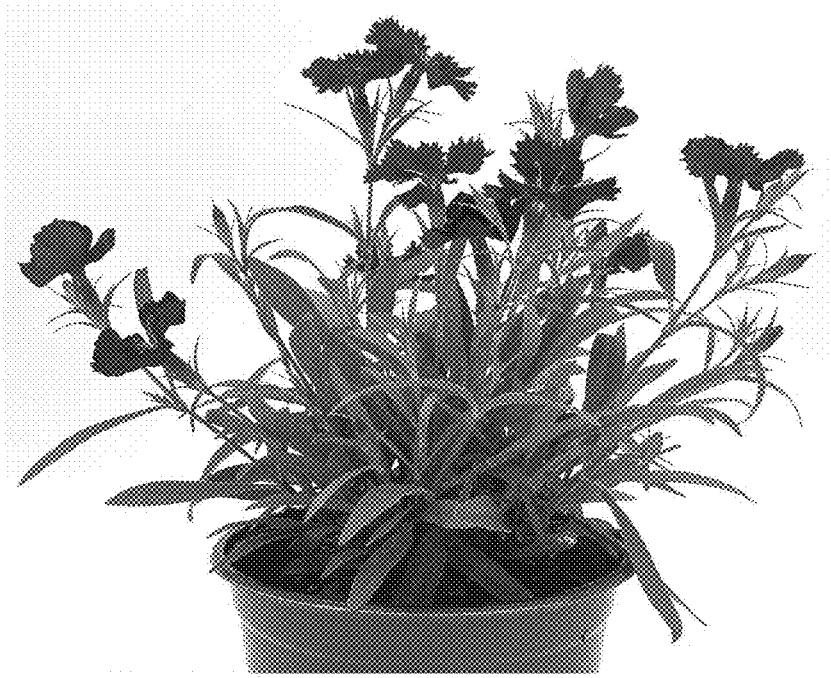

Botanical designation: *Dianthus hybrida.*
Cultivar denomination: 'G21002'.

BACKGROUND OF THE INVENTION

The present invention relates to a new and distinct cultivar of *Dianthus* plant, botanically known as *Dianthus hybrida* and hereinafter referred to by the name 'G21002'.

The new *Dianthus* plant is a product of a planned breeding program conducted by the Inventor in Bellefonte, Pennsylvania. The objective of the breeding program is to create new compact and dense *Dianthus* plants with continuous flowering habit, high temperature tolerance and winter hardiness.

The new *Dianthus* plant originated from a cross-pollination in Bellefonte, Pennsylvania In January 2020 of a proprietary seedling selection of *Dianthus hybrida* identified as code number 51472-3, not patented, as the female, or seed, parent with a proprietary seedling selection of *Dianthus hybrida* identified as code number 54178-2A, not patented, as the male, or pollen, parent. The new *Dianthus* plant was discovered and selected by the Inventor as a single flowering plant from within the progeny of the stated cross-pollination in a controlled environment in Bellefonte, Pennsylvania in July 2020.

Asexual reproduction of the new cultivar by vegetative cuttings in a controlled environment in Bellefonte, Pennsylvania since September 2020 has shown that the unique features of this new *Dianthus* plant are stable and reproduced true to type in successive generations.

SUMMARY OF THE INVENTION

Plants of the new *Dianthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G21002'. These characteristics in combination distinguish 'G21002' as a new and distinct *Dianthus* plant:

1. Compact and mounding plant habit.
2. Vigorous growth habit and rapid growth rate.
3. Freely branching habit; dense and bushy appearance.
4. Dark green-colored leaves.
5. Freely flowering habit.
6. Relatively large single-type dark scarlet red-colored flowers.
7. Good garden performance and winter hardiness.

Plants of the new *Dianthus* can be compared to plants of the female parent selection. In side-by-side comparisons, plants of the new *Dianthus* differ primarily from plants of the female parent selection in the following characteristics:

1. Plants of the new *Dianthus* are larger and more vigorous than plants of the female parent selection.
2. Plants of the new *Dianthus* have larger flowers than plants of the female parent selection.
3. Plants of the new *Dianthus* flower more continuously than plants of the female parent selection.
4. Flowers of plants of the new *Dianthus* are dark scarlet red in color whereas flowers of plants of the female parent selection are burgundy in color.
5. Plants of the new *Dianthus* have not been observed to produce seeds whereas plants of the female parent selection have been observed to produce seeds.

Plants of the new *Dianthus* can be compared to plants of the male parent selection. In side-by-side comparisons, plants of the new *Dianthus* differ primarily from plants of the male parent selection in the following characteristics:

1. Plants of the new *Dianthus* are more compact and denser than plants of the male parent selection.
2. Plants of the new *Dianthus* flower more continuously than plants of the male parent selection.
3. Flowers of plants of the new *Dianthus* are darker scarlet red in color than flowers of plants of the male parent selection.
4. Plants of the new *Dianthus* have not been observed to produce seeds whereas plants of the male parent selection have been observed to produce seeds.

Plants of the new *Dianthus* can be compared to plants of *Dianthus hybrida* 'G19159', disclosed in U.S. Plant Pat. No. 36,710. In side-by-side comparisons, plants of the new *Dianthus* differ primarily from plants of 'G19159' in the following characteristics:

1. Plants of the new *Dianthus* are more compact than plants of 'G19159'.
2. Plants of the new *Dianthus* have single-type flowers whereas plants of 'G19159' have double-type flowers.
3. Flowers of plants of the new *Dianthus* are dark scarlet red in color whereas flowers of plants of 'G19159' are bright magenta in color.

BRIEF DESCRIPTION OF THE PHOTOGRAPHS

The accompanying colored photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the actual colors of the new *Dianthus* plant.

The photograph on the first sheet (FIG. 1) is a side perspective view of a typical flowering plant of 'G21002' grown in a container.

Figure 2:
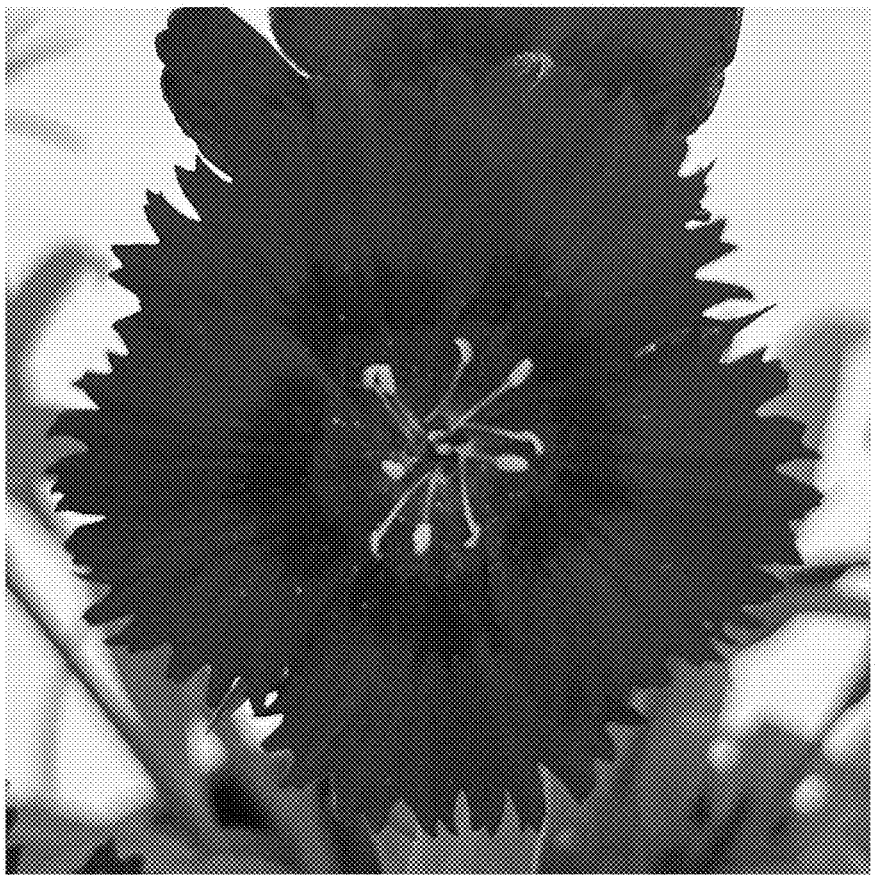

The photograph on the second sheet (FIG. 2) is a close-up view of a typical flower of 'G21002'.

DETAILED BOTANICAL DESCRIPTION

The aforementioned photographs and following observations and measurements describe plants grown during the late summer to early autumn in 740-ml containers in a glass-covered greenhouse in Loudon, New Hampshire and under cultural practices typical of commercial *Dianthus* production. During the production of the plants, day temperatures ranged from 18° C. to 20° C. and night temperatures ranged from 16° C. to 18° C. Plants were pinched one time and were eight weeks from planting rooted young plants when the photographs and description were taken. In the following description, color references are made to The Royal Horticultural Society Colour Chart, 2015 Edition, except where general terms of ordinary dictionary significance are used.

Botanical classification: *Dianthus hybrida* 'G21002'.

Parentage:

*Female, or seed, parent*.—Proprietary seedling selection of *Dianthus hybrida* identified as code number 51472-3, not patented.

*Male, or pollen, parent*.—Proprietary seedling selection of *Dianthus hybrida* identified as code number 541782A, not patented.

Propagation:

*Type*.—By vegetative cuttings.

*Time to initiate roots, summer*.—About 10 to 14 days at soil temperatures about 22.2° C. and ambient temperatures about 18.3° C.

*Time to initiate roots, winter*.—About two to three weeks at soil temperatures about 22.2° C. and ambient temperatures about 18.3° C.

*Time to produce a rooted young plant from an unrooted cutting, summer*.—About five to six weeks at soil temperatures about 22.2° C. and ambient temperatures about 18.3° C.

*Time to produce a rooted young plant from an unrooted cutting, winter*.—About six to eight weeks at soil temperatures about 22.2° C. and ambient temperatures about 18.3° C.

*Root description*.—Medium in thickness and fibrous; typically white to creamy white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; relatively compact and mounding plant habit; vigorous growth habit and rapid growth rate; freely branching habit; dense and bushy appearance.

*Branching habit*.—Freely basal branching with about 15 to 17 primary lateral branches with secondary branches potentially developing at every node.

*Plant height*.—About 13 cm to 15 cm.

*Plant diameter or spread*.—About 20 cm to 22 cm.

*Primary branch description*.—Length: About 13 cm to 15 cm. Diameter: About 2 mm. Internode length: About 3.25 cm to 3.5 cm. Shape: Rounded. Strength: Strong. Aspect: Erect to about 25° to 30° from vertical. Texture and luster: Dense minute pubescence; matte. Color, developing and developed: Close to 146A.

Leaf description:

*Arrangement*.—Opposite, simple; sessile.

*Length*.—About 7.5 cm to 8 cm.

*Width*.—About 1.3 cm to 1.5 cm.

*Shape*.—Linear.

*Apex*.—Acuminate.

*Base*.—Clasping.

*Margin*.—Entire; not undulate.

*Texture and luster, upper and lower surfaces*.—Smooth, glabrous; slightly glossy.

*Venation pattern*.—Pinnate and reticulate.

*Color*.—Developing leaves, upper surface: Close to 146A. Developing leaves, lower surface: Close to 146B. Fully expanded leaves, upper surface: Close to 147A; venation, close to 147A. Fully expanded leaves, lower surface: Close to 146A; venation, close to 146A.

Flower description:

*Flower arrangement and shape*.—Relatively large single-type terminal and axillary flowers; freely flowering habit with about 25 to 30 open flowers per plant at one time; flowering continuous during the flowering season; flowers face upright to slightly outwardly.

*Fragrance*.—Slightly fragrant; clove-like, sweet.

*Natural flowering season*.—Early flowering habit, depending on temperature, plants begin flowering about seven to eight weeks after planting rooted young plants; plants flower from spring until the autumn in New Hampshire; depending on temperature, individual flowers last bout five to seven days on the plant; flowers persistent.

*Flower buds*.—Length: About 1,6 cm. Diameter: About 2 mm. Shape: Oblong; styles not extruded. Texture and luster: Smooth, glabrous; matte. Color, sepals: Close to 146A.

*Flower diameter*.—About 3.5 cm to 3.75 cm.

*Flower depth*.—About 2.75 cm.

*Petals*.—Arrangement: Five petals in a single whorl; petals fused towards the base into a narrow tube. Length: About 1.75 cm to 1.8 cm. Width: About 1.75 cm. Shape: Roughly spatulate. Apex and margin: Praemorse; slightly ruffled. Base: Acute. Texture and luster, upper and lower surfaces: Smooth, glabrous; velvety; matte. Texture and luster, throat: Smooth, glabrous; semi-glossy. Texture and luster, tube: Smooth, glabrous; matte. Color: When developing and fully developed, upper surface: Close to 53A; proximal band, close to 59A; throat, close to 157A to 157B; venation, similar to lamina colors; colors do not change with subsequent development. When developing and fully developed, lower surface: Close to 59B; tube, close to 157A to 157B; venation, similar to lamina colors; colors do not change with subsequent development.

*Sepals*.—Arrangement: Five sepals fused to form an elongate tubular calyx; proximal 70% portion of the sepals are fused. Length: About 2 cm. Width, free part: About 2 mm. Shape: Roughly linear; fused. Apex: Acuminate. Margin, free part: Entire. Texture and luster, upper and lower surfaces: Smooth, glabrous; matte. Color: When opening, upper and lower surfaces: Close to 146A. Fully opened, upper and lower surfaces: Proximally, close to 146A and distally, close to 146A variably tinged with close to 59A.

*Peduncles*.—Length: About 2.3 mm to 2.7 mm. Diameter: About 2 mm. Strength: Strong, wiry; flexible. Aspect: Erect to about 30° from lateral branch axis. Texture and luster: Smooth, glabrous; matte. Color: Close to between 144A and 146A.

*Reproductive organs*.—Stamens: Quantity per flower: About ten. Filament length: About 2 cm. Filament color: Close to 157C. Anther shape: Narrowly oblong. Anther length: About 1 mm. Anther color: Close to 58A, dull. Pollen amount: None observed. Pistils: Quantity per flower: Two. Pistil length: About 2.5 cm. Stigma shape: Pointed, curled outwardly. Stigma color: Close to NN155A. Style length: About 1.8 cm to 2 cm. Style color: Close to NN155A. Ovary shape: Ovoid. Ovary texture: Smooth, glabrous. Ovary color: Close to 144A to 144B.

*Seeds and fruits*.—To date, seed and fruit production has not been observed on plants of the new *Dianthus*.

Pathogen & pest resistance: To date, plants of the new *Dianthus* have not been noted to be resistant to pathogens and pests common to *Dianthus* plants.

Garden performance: Plants of the new *Dianthus* have exhibited good garden performance, to tolerate rain, wind, high temperatures and to be winter-hardy to USDA Hardiness Zone 5.

It is claimed:

1. A new and distinct *Dianthus* plant named 'G21002' as herein illustrated and described.

* * * * *